United States Patent
Schweizer et al.

(10) Patent No.: US 9,629,381 B2
(45) Date of Patent: Apr. 25, 2017

(54) PRODUCTION OF SOLUBLE SOY PROTEIN PRODUCT ("S704")

(75) Inventors: Martin Schweizer, Winnipeg (CA); Kevin I. Segall, Winnipeg (CA)

(73) Assignee: BURCON NUTRASCIENCE (MB) Corp., Vancouver, BC ( * ) Notice: Subject to any disclaimer, the term of this patent is extended or adjusted under 35 U.S.C. 154(b) by 0 days.

(21) Appl. No.: 13/474,788

(22) Filed: May 18, 2012

(65) Prior Publication Data

US 2012/0295008 A1  Nov. 22, 2012

Related U.S. Application Data

(60) Provisional application No. 61/457,721, filed on May 19, 2011, provisional application No. 61/457,815, filed on Jun. 9, 2011.

(51) Int. Cl.

| | | |
|---|---|---|
| *A23L 2/38* | (2006.01) | |
| *A23J 3/16* | (2006.01) | |
| *C07K 14/415* | (2006.01) | |
| *A23L 2/66* | (2006.01) | |
| *A23J 1/14* | (2006.01) | |
| *A23L 11/00* | (2016.01) | |
| *A23L 33/185* | (2016.01) | |

(52) U.S. Cl.
CPC . *A23J 3/16* (2013.01); *A23J 1/14* (2013.01); *A23L 2/66* (2013.01); *A23L 11/07* (2016.08); *A23L 33/185* (2016.08); *C07K 14/415* (2013.01)

(58) Field of Classification Search
CPC .......... C07K 1/14; C07K 1/34; C07K 14/415; A23L 2/66
USPC ....................................................... 426/598
See application file for complete search history.

(56) References Cited

U.S. PATENT DOCUMENTS

| | | | | |
|---|---|---|---|---|
| 3,733,207 | A | * | 5/1973 | McCabe .......................... 426/46 |
| 3,736,147 | A | * | 5/1973 | Okubo ...................... A23J 1/14 |
| | | | | 426/271 |
| 4,208,323 | A | * | 6/1980 | Murray et al. ................ 530/372 |
| 5,844,086 | A | | 12/1998 | Murray |
| 6,005,076 | A | | 12/1999 | Murray |
| 8,389,040 | B2 | | 3/2013 | Schweizer et al. |
| 8,409,654 | B2 | | 4/2013 | Segall et al. |
| 8,501,265 | B2 | | 8/2013 | Segall et al. |
| 8,557,321 | B2 | | 10/2013 | Segall et al. |
| 8,563,071 | B2 | | 10/2013 | Schweizer et al. |
| 2010/0098818 | A1 | | 4/2010 | Schweizer et al. |

FOREIGN PATENT DOCUMENTS

| | | |
|---|---|---|
| CA | 2741120 | 4/2010 |
| CA | 2765745 | 1/2011 |
| WO | WO2010/045727 | 4/2010 |

OTHER PUBLICATIONS

Schweizer: WO/2010/045727; filed Oct. 21, 2009; published Apr. 29, 2010.*
Hayslip: Dispersibility Indices, Emulsion Capacities, and Electrophoretic Comparisons of Protein Extracted From Defatted Soy Flake Suspensions at pH 4.5, pH 3.0, and pH 3.0 in the Presence of Calcium Chloride; Texas Tech University; May 1980.*
Kappos: Under Secretary, David Kappos, titled: "Top 10" tips for improving patent prosecution, of Monday, Jun. 28, 2010; http://usptoexec/US/blog/Lists/Posts/Post.aspx?List=7cf650f8%2De0cf%2D4b72%2D9f%2D47765c02fbe9&ID=56&Source=http%3A%2F%2Fusptoexec%2FUS%2Fblog%2FLists%2FPosts%2FCalendar%2Easpx%3FCalendarDate%3D6%252F28%252F2010.*

* cited by examiner

*Primary Examiner* — Patricia George

(57) ABSTRACT

A soy protein product is obtained by extracting a soy protein source material with an aqueous calcium salt solution to form an aqueous soy protein solution and adjusting the pH of the mixture of aqueous soy protein solution and residual soy protein source to a pH of about 1.5 to about 4.4. The acidified soy protein solution then is separated from the residual soy protein source. The acidified soy protein solution may be dried, following optional concentration and diafiltration, to provide the soy protein product.

57 Claims, No Drawings

PRODUCTION OF SOLUBLE SOY PROTEIN PRODUCT ("S704")

REFERENCE TO RELATED APPLICATIONS

This application claims priority under 35 USC 119(e) from U.S. Provisional Patent Application Nos. 61/457,721 filed May 19, 2011 and 61/457,815 filed Jun. 9, 2011.

FIELD OF INVENTION

The present invention is directed to the production of soy protein products.

BACKGROUND TO THE INVENTION

In U.S. patent application Ser. No. 12/603,087 filed Oct. 21, 2009 (US Patent Publication No. 2010-0098818) and Ser. No. 12/923,897 filed Oct. 13, 2010 (US Patent Publication No. 2011-0038993), assigned to the assignee hereof and the disclosures of which are incorporated herein by reference, there is described the preparation of a soy protein product, preferably a soy protein isolate, which is completely soluble and is capable of providing transparent and heat-stable solutions at low pH values. This protein product may be used for protein fortification of, in particular, soft drinks and sport drinks, as well as other acidic aqueous systems, without precipitation of protein. The soy protein product is produced by extracting a soy protein source with aqueous calcium chloride solution at natural pH, optionally diluting the resulting aqueous soy protein solution, adjusting the pH of the aqueous soy protein solution to a pH of about 1.5 to about 4.4, preferably about 2.0 to about 4.0, to produce an acidified clear soy protein solution, which may be optionally concentrated and diafiltered prior to drying.

SUMMARY OF INVENTION

It has now been found that soy protein products of similar properties to those produced according to the above-noted applications can be prepared if the optional dilution and acidification steps are effected prior to separation of the soy protein solution from the residual soy protein source material.

However, unlike the soy protein product produced as described in the aforementioned applications, the product produced in accordance with the present invention has a notable phytic acid content which may be responsible for the somewhat inferior solution properties exhibited by the soy protein product produced herein in comparison to the soy protein product produced in the aforementioned applications.

In accordance with one aspect of the present invention, there is provided a process of producing a soy protein product having a soy protein content of at least about 60 wt % (N×6.25) on a dry weight basis, which comprises:
 (a) extracting a soy protein source with an aqueous calcium chloride solution to cause solubilization of soy protein from the protein source and to form an aqueous soy protein solution,
 (b) optionally diluting the mixture of aqueous soy protein solution and residual soy protein source,
 (c) adjusting the pH of the mixture of aqueous soy protein solution and residual soy protein source to a pH of about 1.5 to about 4.4, preferably about 2 to about 4,
 (d) separating the acidified aqueous soy protein solution from the residual soy protein source,
 (e) optionally concentrating the acidified aqueous soy protein solution while maintaining the ionic strength substantially constant by using a selective membrane technique,
 (f) optionally diafiltering the concentrated soy protein solution, and
 (g) optionally drying the concentrated soy protein solution.

The soy protein product preferably is an isolate having a protein content of at least about 90 wt %, preferably at least about 100 wt %, (N×6.25) d.b.

The present invention further provides a soy protein product, preferably a soy protein isolate, which is water soluble and forms heat stable solutions at acid pH values and is useful for the protein fortification of aqueous systems, including soft drinks and sports drinks. The soy protein in the product is not hydrolyzed.

The soy protein product provided herein may be provided as an aqueous solution thereof having an acceptable degree of clarity at acid pH values and which is heat stable at these pH values.

The soy protein product can be blended with powdered drinks for the formation of aqueous soft drinks or sports drinks by dissolving the same in water. Such blend may be a powdered beverage.

While the present invention refers mainly to the production of soy protein isolate, it is contemplated that soy protein products of lesser purity may be provided having similar properties to the soy protein isolate. Such lesser purity products may have a protein concentration of at least about 60% by weight (N×6.25) d.b.

In another aspect of the present invention, there is provided an aqueous solution of the soy product provided herein which is heat stable at low pH. The aqueous solution may be a beverage.

The soy protein product produced according to the process herein lacks the characteristic beany flavour of soy protein products and is suitable, not only for protein fortification of acid media, but may be used in a wide variety of conventional applications of protein products, including but not limited to protein fortification of processed foods and beverages, emulsification of oils, as a body former in baked goods and foaming agent in products which entrap gases. In addition, the soy protein product may be formed into protein fibers, useful in meat analogs and may be used as an egg white substitute or extender in food products where egg white is used as a binder. The soy protein product may also be used in nutritional supplements. The soy protein product may also be used in dairy analogue products or products that are dairy/soy blends. Other uses of the soy protein product are in pet foods, animal feed and in industrial and cosmetic applications and in personal care products.

GENERAL DESCRIPTION OF INVENTION

The initial step of the process of providing the soy protein product involves solubilizing soy protein from a soy protein source. The soy protein source may be soybeans or any soy product or by-product derived from the processing of soybeans, including but not limited to soy meal, soy flakes, soy grits and soy flour. The soy protein source may be used in the full fat form, partially defatted form or fully defatted form. Where the soy protein source contains an appreciable amount of fat, an oil-removal step generally is required during the process. The soy protein recovered from the soy protein source may be the protein naturally occurring in soybean or the proteinaceous material may be a protein modified by genetic manipulation but possessing characteristic hydrophobic and polar properties of the natural protein.

Protein solubilization from the soy protein source material is effected most conveniently using calcium chloride solution, although solutions of other calcium salts, may be used. In addition, other alkaline earth metal compounds may be used, such as magnesium salts. Further, extraction of the soy protein from the soy protein source may be effected using calcium salt solution in combination with another salt solution, such as sodium chloride. Additionally, extraction of the soy protein from the soy protein source may be effected using water or other salt solution, such as sodium chloride, with calcium salt subsequently being added to the aqueous soy protein solution produced in the extraction step. Precipitate formed upon addition of the calcium salt is removed prior to subsequent processing.

As the concentration of the calcium salt solution increases, the degree of solubilization of protein from the soy protein source initially increases until a maximum value is achieved. Any subsequent increase in salt concentration does not increase the total protein solubilized. The concentration of calcium salt solution which causes maximum protein solubilization varies depending on the salt concerned. It is usually preferred to utilize a concentration value less than about 1.0 M, and more preferably a value of about 0.10 to about 0.15 M.

In a batch process, the salt solubilization of the protein is effected at a temperature of from about 1° C. to about 100° C., preferably about 15° to about 65° C., more preferably about 50° C. to about 60° C., preferably accompanied by agitation to decrease the solubilization time, which is usually about 1 to about 60 minutes. It is preferred to effect the solubilization to extract substantially as much protein from the soy protein source as is practicable, so as to provide an overall high product yield.

In a continuous process, the extraction of the soy protein from the soy protein source is carried out in any manner consistent with effecting a continuous extraction of soy protein from the soy protein source. In one embodiment, the soy protein source is continuously mixed with the calcium salt solution and the mixture is conveyed through a pipe or conduit having a length and at a flow rate for a residence time sufficient to effect the desired extraction in accordance with the parameters described herein. In such a continuous procedure, the salt solubilization step is effected in a time of about 1 to about 60 minutes, preferably to effect solubilization to extract substantially as much protein from the soy protein source as is practicable. The solubilization in the continuous procedure is effected at temperatures between about 1° C. and about 100° C., preferably about 15° to about 65° C., more preferably between about 50° C. and about 60° C.

The extraction is generally conducted at a pH of about 4.5 to about 11, preferably about 5 to about 7. The pH of the extraction system (soy protein source and calcium salt solution) may be adjusted to any desired value within the range of about 4.5 to about 11 for use in the extraction step by the use of any convenient food grade acid, usually hydrochloric acid or phosphoric acid, or food grade alkali, usually sodium hydroxide, as required.

The concentration of soy protein source in the calcium salt solution during the solubilization step may vary widely. Typical concentration values are about 5 to about 15% w/v.

The protein extraction step with the aqueous salt solution has the additional effect of solubilizing fats which may be present in the soy protein source, which then results in the fats being present in the aqueous phase.

The protein solution resulting from the extraction step generally has a protein concentration of about 5 to about 50 g/L, preferably about 10 to about 50 g/L.

The aqueous calcium salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of any phenolics in the protein solution.

The mixture of aqueous soy protein solution and residual soy protein source may be diluted generally with about 0.5 to about 10 volumes, preferably about 0.5 to about 2 volumes, of aqueous diluent in order to decrease the conductivity of the mixture to a value of generally below about 90 mS, preferably about 2 to about 18 mS. Such dilution is usually effected using water, although dilute salt solution, such as sodium chloride or calcium chloride, having a conductivity of up to about 3 mS, may be used.

The diluent with which the combined soy protein solution and residual soy protein source is mixed generally has the same temperature as the mixture of soy protein solution and residual soy protein source, but the diluent may have a temperature of about 1° to about 100° C., preferably about 15° to about 65° C., more preferably about 50° to about 60° C.

The optionally diluted mixture of soy protein solution and residual soy protein source then is adjusted in pH to a value of about 1.5 to about 4.4, preferably about 2 to about 4, by the addition of any suitable food grade acid. The acidified mixture has a conductivity of generally below about 95 mS for a diluted mixture or generally below about 115 mS for an undiluted mixture, in both cases preferably about 2 to about 23 mS.

The acidified aqueous protein solution is then separated from the residual soy protein source, in any convenient manner, such as by employing a decanter centrifuge or any suitable sieve, followed by disc centrifugation and/or filtration, to remove residual soy protein source material. The separation step is generally conducted at the temperature of the optionally diluted, pH adjusted mixture of soy protein solution and residual soy protein material, but may be conducted at any temperature within the range of about 1° to about 100° C., preferably about 15° to about 65° C., more preferably about 50° C. to about 60° C. The separated residual soy protein source may be dried for disposal. Alternatively, the separated residual soy protein source may be processed to recover some residual protein. The separated residual soy protein source may be processed by a conventional isoelectric precipitation procedure or any other convenient procedure to recover residual protein.

Where the soy protein source contains significant quantities of fat, as described in U.S. Pat. Nos. 5,844,086 and 6,005,076, assigned to the assignee hereof and the disclosures of which are incorporated herein by reference, then the defatting steps described therein may be effected on the aqueous protein solution. Alternatively, defatting of the separated aqueous protein solution may be achieved by any other convenient procedure.

The acidified aqueous soy protein solution may be subjected to a heat treatment to inactivate heat labile anti-nutritional factors, such as trypsin inhibitors, present in such solution as a result of extraction from the soy protein source material during the extraction step. Such a heating step also provides the additional benefit of reducing the microbial load. Generally, the protein solution is heated to a temperature of about 70° to about 160° C., for about 10 seconds to about 60 minutes, preferably about 80° to about 120° C. for about 10 seconds to about 5 minutes, more preferably about 85° to about 95° C., for about 30 seconds to about 5 minutes. The heat treated acidified soy protein solution then may be cooled for further processing as described below, to a temperature of about 2° to about 65° C., preferably about 50° C. to about 60° C.

Alternatively, this heat treatment step may be carried out prior to the separation of the acidified aqueous protein solution from the residual soy protein source described above.

The acidified aqueous soy protein solution may be treated with an adsorbent, such as powdered activated carbon or granulated activated carbon, to remove colour and/or odour compounds. Such adsorbent treatment may be carried out under any convenient conditions, generally at the ambient temperature of the separated aqueous protein solution. For powdered activated carbon, an amount of about 0.025% to about 5% w/v, preferably about 0.05% to about 2% w/v, is employed. The adsorbing agent may be removed from the soy solution by any convenient means, such as by filtration.

The optionally defatted, optionally heat treated and optionally adsorbent treated acidified aqueous soy protein solution may optionally be polished by any convenient means, such as by filtering, to remove any residual particulates.

The resulting acidified aqueous soy protein solution may be directly dried to produce a soy protein product. In order to provide a soy protein product having a decreased impurities content and a reduced salt content, such as a soy protein isolate, the acidified aqueous soy protein solution may be processed prior to drying.

The acidified aqueous soy protein solution may be concentrated to increase the protein concentration thereof while maintaining the ionic strength thereof substantially constant. Such concentration generally is effected to provide a concentrated soy protein solution having a protein concentration of about 50 to about 300 g/L, preferably about 100 to about 200 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 1,000,000 Daltons, preferably about 5,000 to about 100,000 Daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as carbohydrates, pigments, low molecular weight proteins and anti-nutritional factors, such as trypsin inhibitors, which are themselves low molecular weight proteins. The molecular weight cut-off of the membrane is usually chosen to ensure retention of a significant proportion of the protein in the solution, while permitting contaminants to pass through having regard to the different membrane materials and configurations.

The concentrated soy protein solution then may be subjected to a diafiltration step using water or a dilute saline solution. The diafiltration solution may be at its natural pH or at a pH equal to that of the protein solution being diafiltered or at any pH value in between. Such diafiltration may be effected using from about 1 to about 40 volumes of diafiltration solution, preferably about 2 to about 25 volumes of diafiltration solution. In the diafiltration operation, further quantities of contaminants are removed from the aqueous soy protein solution by passage through the membrane with the permeate. This purifies the aqueous protein solution and may also reduce its viscosity. The diafiltration operation may be effected until no significant further quantities of contaminants or visible colour are present in the permeate or until the retentate has been sufficiently purified so as, when dried, to provide a soy protein isolate with a protein content of at least about 90 wt % (N×6.25) d.b. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 1,000,000 Daltons, preferably about 5,000 to about 100,000 Daltons, having regard to different membrane materials and configuration.

Alternatively, the diafiltration step may be applied to the acidified aqueous protein solution prior to concentration or to the partially concentrated acidified aqueous protein solution. Diafiltration may also be applied at multiple points during the concentration process. When diafiltration is applied prior to concentration or to the partially concentrated solution, the resulting diafiltered solution may then be additionally concentrated. The viscosity reduction achieved by diafiltering multiple times as the protein solution is concentrated may allow a higher final, fully concentrated protein concentration to be achieved. This reduces the volume of material to be dried.

The concentration step and the diafiltration step may be effected herein in such a manner that the soy protein product subsequently recovered contains less than about 90 wt % protein (N×6.25) d.b., such as at least about 60 wt % protein (N×6.25) d.b. By partially concentrating and/or partially diafiltering the aqueous soy protein solution, it is possible to only partially remove contaminants. This protein solution may then be dried to provide a soy protein product with lower levels of purity. The soy protein product is still able to produce heat stable protein solutions under acidic conditions.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit the oxidation of any phenolics present in the soy protein solution.

The concentration step and the optional diafiltration step may be effected at any convenient temperature, generally about 2° to about 65° C., preferably about 50° to about 60° C., and for the period of time to effect the desired degree of concentration and diafiltration. The temperature and other conditions used to some degree depend upon the membrane equipment used to effect the membrane processing, the desired protein concentration of the solution and the efficiency of the removal of contaminants to the permeate.

There are two main trypsin inhibitors in soy, namely the Kunitz inhibitor, which is a heat-labile molecule with a molecular weight of approximately 21,000 Daltons, and the Bowman-Birk inhibitor, a more heat-stable molecule with a molecular weight of about 8,000 Daltons. The level of trypsin inhibitor activity in the final soy protein product can be controlled by manipulation of various process variables.

As noted above, heat treatment of the acidified aqueous soy protein solution may be used to inactivate heat-labile trypsin inhibitors. The partially concentrated or fully concentrated acidified aqueous soy protein solution may also be heat treated to inactivate heat labile trypsin inhibitors. When the heat treatment is applied to the partially concentrated acidified aqueous soy protein solution, the resulting heat treated solution may then be additionally concentrated.

In addition, the concentration and/or diafiltration steps may be operated in a manner favorable for removal of trypsin inhibitors in the permeate along with the other contaminants. Removal of the trypsin inhibitors is promoted by using a membrane of larger pore size, such as about 30,000 to about 1,000,000 Da, operating the membrane at elevated temperatures, such as about 30° to about 65° C., preferably 50° to about 60° C. and employing greater volumes of diafiltration medium, such as about 10 to about 40 volumes.

Preparing and membrane processing the protein solution at a lower pH of about 1.5 to about 3 may reduce the trypsin inhibitor activity relative to preparing and processing the solution at higher pH of about 3 to about 4.4. When the protein solution is concentrated and diafiltered at the low end of the pH range, it may be desired to raise the pH of the retentate prior to drying. The pH of the concentrated and diafiltered protein solution may be raised to the desired value, for example pH 3, by the addition of any convenient food grade alkali such as sodium hydroxide.

Further, a reduction in trypsin inhibitor activity may be achieved by exposing soy materials to reducing agents that disrupt or rearrange the disulfide bonds of the inhibitors. Suitable reducing agents include sodium sulfite, cysteine and N-acetylcysteine.

The addition of such reducing agents may be effected at various stages of the overall process. The reducing agent may be added with the soy protein source material in the extraction step, may be added to the aqueous soy protein solution following removal of residual soy protein source material, may be added to the concentrated protein solution before or after diafiltration or may be dry blended with the dried soy protein product. The addition of the reducing agent may be combined with a heat treatment step and the membrane processing steps, as described above.

If it is desired to retain active trypsin inhibitors in the concentrated protein solution, this can be achieved by eliminating or reducing the intensity of the heat treatment step, not utilizing reducing agents, operating the concentration and diafiltration steps at the higher end of the pH range, such as pH 3 to about 4.4, utilizing a concentration and diafiltration membrane with a smaller pore size, operating the membrane at lower temperatures and employing fewer volumes of diafiltration medium.

The concentrated and optionally diafiltered protein solution may be subject to a further defatting operation, if required, as described in U.S. Pat. Nos. 5,844,086 and 6,005,076. Alternatively, defatting of the concentrated and optionally diafiltered protein solution may be achieved by any other convenient procedure.

The concentrated and optionally diafiltered aqueous protein solution may be treated with an adsorbent, such as powdered activated carbon or granulated activated carbon, to remove colour and/or odour compounds. Such adsorbent treatment may be carried out under any convenient conditions, generally at the ambient temperature of the concentrated protein solution. For powdered activated carbon, an amount of about 0.025% to about 5% w/v, preferably about 0.05% to about 2% w/v, is employed. The adsorbent may be removed from the soy protein solution by any convenient means, such as by filtration.

The concentrated and optionally diafiltered aqueous soy protein solution may be dried by any convenient technique, such as spray drying or freeze drying. A pasteurization step may be effected on the soy protein solution prior to drying. Such pasteurization may be effected under any desired pasteurization conditions. Generally, the concentrated and optionally diafiltered soy protein solution is heated to a temperature of about 55° to about 70° C., preferably about 60° to about 65° C., for about 30 seconds to about 60 minutes, preferably about 10 minutes to about 15 minutes. The pasteurized concentrated soy protein solution then may be cooled for drying, preferably to a temperature of about 25° to about 40° C.

The dry soy protein product has a protein content in excess of about 60 wt % (N×6.25) d.b. Preferably, the dry soy protein product is an isolate with a high protein content, in excess of about 90 wt % protein, preferably at least about 100 wt % (N×6.25) d.b.

The soy protein product produced herein is soluble in an acidic aqueous environment, making the product ideal for incorporation into beverages, both carbonated and uncarbonated, to provide protein fortification thereto. Such beverages have a wide range of acidic pH values, ranging from about 2.5 to about 5. The soy protein product provided herein may be added to such beverages in any convenient quantity to provide protein fortification to such beverages, for example, at least about 5 g of the soy protein per serving. The added soy protein product dissolves in the beverage and remains dissolved after thermal processing. The soy protein product may be blended with dried beverage prior to reconstitution of the beverage by dissolution in water. In some cases, modification to the normal formulation of the beverages to tolerate the composition of the invention may be necessary where components present in the beverage may adversely affect the ability of the composition of the invention to remain dissolved in the beverage.

EXAMPLES

Example 1

This Example illustrates the production of a novel soy protein isolate by the method of the invention.

30 kg of defatted soy white flake was added to 300 L of 0.15 M $CaCl_2$ solution at ambient temperature and agitated for 30 minutes to provide an aqueous protein solution. 300 L of reverse osmosis (RO) purified water was added and the pH of the system lowered to about 3 with a solution of HCl. The residual soy white flake was then removed and the resulting protein solution clarified by centrifugation and filtration to provide 520 L of acidified protein solution having a protein content of 1.63% by weight. The acidified solution was heat treated at 90° C. for 30 seconds then cooled to 30° C. for further processing.

The heat treated acidified protein solution was reduced in volume from 520 L to 141 L by concentration on a polyethersulfone membrane, having a molecular weight cutoff of 100,000 Daltons, operated at a temperature of approximately 30° C. At this point the protein solution, with a protein content of 5.02 wt %, was diafiltered with 212 L of RO water, with the diafiltration operation conducted at approximately 30° C. The diafiltered solution was then further concentrated to a volume of 71 L. An aliquot of 31 L of the concentrated protein solution was diafiltered with an additional 225 L of RO water, with the diafiltration operation conducted at approximately 29° C. After this second diafiltration, the protein solution was concentrated from a protein content of 10.12% by weight to a protein content of 12.05% by weight then diluted to a protein content of 6.04% by weight with water to facilitate spray drying. The protein solution before spray drying was recovered in a yield of 38.6 wt % of the initial filtered protein solution. The diafiltered, concentrated and diluted protein solution was then dried to yield a product found to have a protein content of 97.40% (N×6.25) d.b. The product was given designation S017-D12-10A S704H.

A solution of S017-D12-10A S704H was prepared by dissolving sufficient protein powder to supply 0.48 g of protein in 15 ml of reverse osmosis purified water and the colour and clarity assessed using a HunterLab ColorQuest XE instrument operated in transmission mode. The pH of the solution was measured with a pH meter.

The pH, colour and clarity values are set forth in the following Table 1:

TABLE 1 pH and HunterLab readings for 3.2% protein solution of S017-D12-10A S704H

| Sample | pH | L* | a* | b* | haze (%) |
|---|---|---|---|---|---|
| S017-D12-10A S704H | 3.25 | 89.24 | 0.58 | 16.27 | 27.9 |

As may be seen from Table 1, the solution of S017-D12-10A S704H in water was semi-transparent, not transparent.

The colour of the dry powder was also assessed with the HunterLab ColorQuest XE instrument in reflectance mode. The colour values are set forth in the following Table 2:

TABLE 2

HunterLab scores for S017-D12-10A S704H dry powder

| Sample | L* | a* | b* |
|---|---|---|---|
| S017-D12-10A S704H | 88.74 | −0.29 | 8.38 |

As may be seen from Table 2, the dry product was very light in colour.

Example 2

This Example contains an evaluation of the heat stability in water of the soy protein isolate produced by the method of Example 1.

A solution of S017-D12-10A S704H was prepared by dissolving sufficient protein powder to supply 1.6 g of protein in 80 ml of reverse osmosis purified water. The pH of the solution was determined to be 3.37. The sample was split into two portions and the pH of one portion was lowered to 3.00 with HCl solution. The clarity of the control and pH adjusted solutions was assessed by haze measurement with the HunterLab ColorQuest XE instrument. The solutions were then heated to 95° C., held at this temperature for 30 seconds and then immediately cooled to room temperature in an ice bath. The clarity of the heat treated solutions was then measured again.

The clarity of the protein solutions before and after heating is set forth in the following Table 3:

TABLE 3

Effect of heat treatment on clarity of S017-D12-10A S704H solutions

| Sample | Haze before heating (%) | Haze after heating (%) |
|---|---|---|
| pH 3.37 | 55.5 | 25.2 |
| pH 3.00 | 38.5 | 16.9 |

As can be seen from the results in Table 3, it was found that the initial solutions of S017-D12-10A S704H were quite hazy, particularly at the natural pH. However, the solutions were heat stable, with the haze level actually reduced somewhat by the heat treatment.

Example 3

This Example contains an evaluation of the solubility in water of the soy protein isolate produced by the method of Example 1. Solubility was tested based on protein solubility (termed protein method, a modified version of the procedure of Morr et al., J. Food Sci. 50:1715-1718) and total product solubility (termed pellet method).

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. A sample was also prepared at natural pH. For the pH adjusted samples, the pH was measured and corrected periodically during the 60 minutes stirring. After the 60 minutes of stirring, the samples were made up to 50 ml total volume with RO water, yielding a 1% w/v protein dispersion. The protein content of the dispersions was measured using a Leco TruSpec N Nitrogen Determinator. Aliquots (20 ml) of the dispersions were then transferred to pre-weighed centrifuge tubes that had been dried overnight in a 100° C. oven then cooled in a desiccator and the tubes capped. The samples were centrifuged at 7,800 g for 10 minutes, which sedimented insoluble material and yielded a clear supernatant. The protein content of the supernatant was measured by Leco analysis and then the supernatant and the tube lids were discarded and the pellet material dried overnight in an oven set at 100° C. The next morning the tubes were transferred to a desiccator and allowed to cool. The weight of dry pellet material was recorded. The dry weight of the initial protein powder was calculated by multiplying the weight of powder used by a factor of ((100−moisture content of the powder (%))/100). Solubility of the product was then calculated two different ways:

Solubility (protein method) (%)=(% protein in supernatant/% protein in initial dispersion)×100       1)

Solubility (pellet method) (%)=(1−(weight dry insoluble pellet material/((weight of 20 ml of dispersion/weight of 50 ml of dispersion)×initial weight dry protein powder)))×100       2)

The natural pH value of the protein isolate produced in Example 1 in water (1% protein) is shown in Table 4:

TABLE 4

Natural pH of S017-D12-10A S704H solution prepared in water at 1% protein

| Batch | Product | Natural pH |
|---|---|---|
| S017-D12-10A | S704H | 3.43 |

The solubility results obtained are set forth in the following Tables 5 and 6:

TABLE 5

Solubility of S017-D12-10A S704H at different pH values based on protein method

| | | Solubility (protein method) (%) | | | | | | |
|---|---|---|---|---|---|---|---|---|
| Batch | Product | pH 2 | pH 3 | pH 4 | pH 5 | pH 6 | pH 7 | Nat. pH |
| S017-D12-10A | S704H | 98.6 | 99.5 | 53.5 | 2.6 | 12.5 | 74.5 | 85.4 |

TABLE 6

Solubility of S017-D12-10A S704H at different pH values based on pellet method

| | | Solubility (pellet method) (%) | | | | | | |
|---|---|---|---|---|---|---|---|---|
| Batch | Product | pH 2 | pH 3 | pH 4 | pH 5 | pH 6 | pH 7 | Nat. pH |
| S017-D12-10A | S704H | 98.6 | 93.2 | 60.4 | 2.4 | 21.5 | 68.4 | 79.8 |

As can be seen from the results of Tables 5 and 6, the S704H product was extremely soluble at pH 2 and also very soluble at pH 3. The product was not as soluble at higher pH values.

Example 4

This Example contains an evaluation of the clarity in water of the soy protein isolate produced by the method of Example 1.

The clarity of the 1% w/v protein solutions prepared as described in Example 3 was assessed by measuring the absorbance at 600 nm (water blank), with a lower absorbance score indicating greater clarity. Analysis of the samples on a HunterLab ColorQuest XE instrument in transmission mode also provided a percentage haze reading, another measure of clarity.

The clarity results are set forth in the following Tables 7 and 8:

TABLE 7

Clarity of S017-D12-10A S704H solution at different pH values as assessed by A600

| | | A600 | | | | | | |
|---|---|---|---|---|---|---|---|---|
| Batch | Product | pH 2 | pH 3 | pH 4 | pH 5 | pH 6 | pH 7 | Nat. pH |
| S017-D12-10A | S704H | 0.119 | 0.140 | 1.172 | 2.810 | 2.391 | 0.327 | 0.211 |

TABLE 8

Clarity of S017-D12-10A S704H solution at different pH values as assessed by HunterLab analysis

| | | HunterLab haze reading (%) | | | | | | |
|---|---|---|---|---|---|---|---|---|
| Batch | Product | pH 2 | pH 3 | pH 4 | pH 5 | pH 6 | pH 7 | Nat. pH |
| S017-D12-10A | S704H | 22.2 | 27.3 | 94.3 | 97.3 | 97.4 | 71.6 | 43.5 |

As can be seen from the results of Tables 7 and 8, the solutions of S704H were hazy at pH 2 to 3 and cloudier at higher pH values, particularly in the range of 4 to 6.

Example 5

This Example contains an evaluation of the solubility in a soft drink (Sprite) and sports drink (Orange Gatorade) of the soy protein isolate produced by the method of Example 1. The solubility was determined with the protein added to the beverages with no pH correction and again with the pH of the protein fortified beverages adjusted to the level of the original beverages.

When the solubility was assessed with no pH correction, a sufficient amount of protein powder to supply 1 g of protein was weighed into a beaker and a small amount of beverage was added and stirred until a smooth paste formed. Additional beverage was added to bring the volume to 50 ml, and then the solutions were stirred slowly on a magnetic stirrer for 60 minutes to yield a 2% protein w/v dispersion. The protein content of the samples was analyzed using a Leco TruSpec N Nitrogen Determinator then an aliquot of the protein containing beverages was centrifuged at 7,800 g for 10 minutes and the protein content of the supernatant measured.

Solubility (%)=(% protein in supernatant/% protein in initial dispersion)×100

When the solubility was assessed with pH correction, the pH of the soft drink (Sprite) (3.43) and sports drink (Orange Gatorade) (3.09) without protein was measured. A sufficient amount of protein powder to supply 1 g of protein was weighed into a beaker and a small amount of beverage was added and stirred until a smooth paste formed. Additional beverage was added to bring the volume to approximately 45 ml, and then the solutions were stirred slowly on a magnetic stirrer for 60 minutes. The pH of the protein containing beverages was determined immediately after dispersing the protein and was adjusted to the original no-protein pH with HCl or NaOH as necessary. The pH was measured and corrected periodically during the 60 minutes stirring. After the 60 minutes of stirring, the total volume of each solution was brought to 50 ml with additional beverage, yielding a 2% protein w/v dispersion. The protein content of the samples was analyzed using a Leco TruSpec N Nitrogen Determinator then an aliquot of the protein containing beverages was centrifuged at 7,800 g for 10 minutes and the protein content of the supernatant measured.

Solubility (%)=(% protein in supernatant/% protein in initial dispersion)×100

The results obtained are set forth in the following Table 9:

TABLE 9

Solubility of S017-D12-10A S704H in Sprite and Orange Gatorade

| | | No pH correction | | pH correction | |
|---|---|---|---|---|---|
| Batch | Product | Solubility (%) in Sprite | Solubility (%) in Orange Gatorade | Solubility (%) in Sprite | Solubility (%) in Orange Gatorade |
| S017-D12-10A | S704H | 73.3 | 80.7 | 87.2 | 84.1 |

As can be seen from the results of Table 9, the S704H was fairly soluble in the Sprite and the Orange Gatorade. The solubility was somewhat improved by lowering the pH of the protein fortified sample to that of the original beverage without protein.

Example 6

This Example contains an evaluation of the clarity in a soft drink and sports drink of the soy protein isolate produced by the method of Example 1.

The clarity of the 2% w/v protein dispersions prepared in soft drink (Sprite) and sports drink (Orange Gatorade) in Example 5 were assessed using the HunterLab haze method described in Example 4.

The results obtained are set forth in the following Table 10:

TABLE 10

HunterLab haze readings for S017-D12-10A S704H in Sprite and Orange Gatorade

| | | no pH correction | | pH correction | |
|---|---|---|---|---|---|
| Batch | Product | haze (%) in Sprite | haze (%) in Orange Gatorade | haze (%) in Sprite | haze (%) in Orange Gatorade |
| no protein | | 0.0 | 76.6 | 0.0 | 76.6 |
| S017-D12-10A | S704H | 75.9 | 89.8 | 81.8 | 87.9 |

As can be seen from the results of Table 10 the solutions of protein fortified Sprite and Orange Gatorade were quite cloudy.

Example 7

This Example contains an evaluation of the phytic acid content of the soy protein isolate produced by the method of Example 1.

The phytic acid content of the S017-D12-10A S704H was determined by the procedure of Latta and Eskin (J. Agric. Food Chem., 28: 1313-1315). The phytic acid content of the S017-D12-10A S704H was 1.54 wt % d.b.

SUMMARY OF THE DISCLOSURE

In summary of this disclosure, the present invention provides a procedure for the preparation of a soy protein product in which the soy protein source material is not separated from the aqueous soy protein solution until after dilution and acidification. Modifications are possible within the scope of this invention.

What we claim is:

1. A process of producing a soy protein product having a protein content of at least about 60 wt % (N×6.25) on a dry weight basis (d.b.), which comprises:
   (a) extracting a soy protein source, selected from the group consisting of soymeal, soy flakes, soy grits and soy flour with an aqueous calcium chloride solution to cause solubilization of soy protein from the soy protein source and to form a mixture of aqueous soy protein solution and residual soy protein source, wherein said aqueous calcium chloride solution has a concentration of about 0.10 to about 0.15 M and said mixture having a pH of about 4.5 to about 11;
   (b) optionally diluting the mixture of aqueous soy protein solution and residual soy protein source,
   (c) subjecting the mixture of aqueous soy protein solution and residual soy protein source to a pH adjustment step to a pH of about 1.5 to about 4.4 to provide a mixture of an acidified aqueous soy protein solution and residual soy protein source,
   (d) separating the acidified aqueous soy protein solution from the residual soy protein source,
   (e) concentrating the acidified aqueous soy protein solution while maintaining the ionic strength substantially constant using a selective membrane technique to form a concentrated soy protein solution,
   (f) optionally diafiltering the concentrated soy protein solution, wherein said concentration step and optional diafiltration step are effected until the concentrated and optionally diafiltered soy protein solution has been sufficiently purified so as, when dried, to provide a soy protein product with a protein source of at least about 60 wt % (N×6.25) d.b., and (g) drying the optionally diafiltered and concentrated soy protein solution to provide a soy protein product having a soy protein content of at least about 60 wt % (N×6.25) d.b., and
   (g) drying the optionally diafiltered and concentrated soy protein solution to provide a soy protein product having a soy protein content of at least about 60 wt % (N×6.25) d.b.

2. The process of claim 1 wherein said extraction step is effected using an aqueous calcium chloride solution having a concentration of less than about 1.0 M.

3. The process of claim 1 wherein said extraction step is effected et a temperature of about 15° to about 65° C.

4. The process of claim 1 wherein said aqueous soy protein solution has a protein concentration of about 5 to about 50 g/L.

5. The process of claim 1 wherein said aqueous calcium salt solution contains an antioxidant.

6. The process of claim 1 wherein, following said extraction step and prior to said pH adjustment step, said mixture of aqueous soy protein solution and residual soy protein source is diluted to a conductivity of less than about 90 mS.

7. The process of claim 6 wherein said mixture of aqueous soy protein solution and residual soy protein source is diluted with about 0.5 to about 10 volumes of aqueous diluent.

8. The process of claim 7 wherein said mixture of aqueous soy protein solution and residual soy protein source is diluted with about 0.5 to about 2 volumes of aqueous diluent.

9. The process of claim 6 wherein said mixture of aqueous soy protein solution and residual soy protein source is diluted to a conductivity of about 2 to about 18 mS.

10. The process of claim 6 wherein said aqueous diluent has a temperature of about 15° to about 65° C.

11. The process of claim 1 wherein the pH of said optionally diluted mixture of aqueous soy protein solution and residual soy protein source is adjusted to about pH 2 to about 4.

12. The process of claim 1 wherein said acidified mixture of soy protein solution and residual soy protein source has a conductivity of less than about 95 mS.

13. The process of claim 1 wherein the acidified mixture of soy protein solution and residual soy protein source, prior to said separating step is subjected to a heat treatment step to inactivate heat-labile trypsin inhibitors.

14. The process of claim 13, wherein said heat treatment is effected at a temperature of about 70° to about 160° C. for about 10 seconds to about 60 minutes.

15. The process of claim 13 wherein the heat treated acidified mixture of soy protein solution and residual soy protein source is cooled to a temperature of about 2° to about 65° C. for further processing.

16. The process of claim 1, wherein following said separation step, the acidified aqueous protein solution is subjected to a heat treatment step to inactivate heat-labile, including heat-labile trypsin inhibitors, and also preferably pasteurizes the acidified aqueous protein solution.

17. The process of claim 16, wherein said heat treatment is effected at a temperature of about 70° to about 160° C. for about 10 seconds to about 60 minutes.

18. The process of claim 16 wherein the heat treated acidified soy protein solution is cooled to a temperature of about 2° to about 65° C. for further processing.

19. The process of claim 1 wherein following said separating step, the acidified aqueous soy protein solution is treated with an adsorbent to remove colour and/or odour compounds from the acidic aqueous soy protein solution.

20. The process of claim 1 wherein the acidified aqueous soy protein solution is subjected to a polishing step.

21. The process of claim 1 wherein said acidified aqueous soy protein solution is concentrated while maintaining the ionic strength thereof substantially constant to produce a concentrated acidified soy protein solution having a protein concentration of about 50 to about 300 g/L.

22. The process of claim 21 wherein said concentrated acidified aqueous soy protein solution has a protein concentration of about 100 to about 200 g/L.

23. The process of claim 21 wherein said concentration step is effected by ultrafiltration using a membrane having a molecular weight cut-off of about 3,000 to about 1,000,000 daltons.

24. The process of claim 21 wherein a diafiltration step is effected using water, acidified water, dilute saline or acidified dilute saline on the acidified soy protein solution before or after partial or complete concentration thereof.

25. The process of claim 24 wherein said diafiltration is effected using about 1 to about 40 volumes of diafiltration solution.

26. The process of claim 24 wherein said diafiltration is effected until no significant further quantities of contaminants or visible colour are present in the permeate.

27. The process of claim 24 wherein said diafiltration is effected until the retentate has been sufficiently purified so as, when dried, to provide a soy protein isolate with a protein content of at least about 90 wt % (N×6.25) d.b.

28. The process of claim 24 wherein said diafiltration is effected using a membrane having a molecular weight cut-off of about 3,000 to about 1,000,000 Daltons.

29. The process of claim 21 wherein said concentration step and optional diafiltration step are carried out at a temperature of about 2° to about 65° C.

30. The process of claim 21 wherein partially concentrated or concentrated and optionally diafiltered acidified aqueous soy protein solution is subjected to a heat treatment step to inactivate heat-labile trypsin inhibitors.

31. The process of claim 30 wherein said heat treatment is effected at a temperature of about 70° to about 160° C. for about 10 seconds to about 60 minutes.

32. The process of claim 30 wherein the heat treated soy protein solution is cooled to a temperature of about 2° to about 65° C. for further processing.

33. The process of claim 21 wherein said concentrated and optionally diafiltered acidified aqueous soy protein solution is treated with an adsorbent to remove colour and/or odour compounds.

34. The process of claim 21 wherein said concentrated and optionally diafiltered acidified aqueous soy protein solution is pasteurized prior to drying.

35. The process of claim 34 wherein said pasteurization step is effected at a temperature of about 55° to about 70° C. for about 30 seconds to about 60 minutes.

36. The process of claim 27 wherein said concentrated and diafiltered acidified aqueous soy protein solution is dried to provide a soy protein isolate having a protein content of at least about 90 wt % (N×6.25) d.b.

37. The process of claim 36 wherein said soy protein isolate has a protein content of at least about 100 wt % (N×6.25) d.b.

38. The process of claim 21 wherein the concentration and/or optional diafiltration step are operated in a manner favourable to the removal of trypsin inhibitors.

39. The process of claim 1 wherein a reducing agent is present during the extraction step to disrupt or rearrange the disulfide bonds of trypsin inhibitors to achieve a reduction in trypsin inhibitor activity.

40. The process of claim 21 wherein a reducing agent is present during the concentration and/or optional diafiltration step to disrupt or rearrange the disulfide bonds of trypsin inhibitors to achieve a reduction in trypsin inhibitor activity.

41. The process of claim 1 wherein a reducing agent is added to the concentrated and optionally diafiltered soy protein solution prior to drying and/or the dried soy protein product to disrupt or rearrange the disulfide bonds of trypsin inhibitors to achieve a reduction in trypsin inhibitor activity.

42. The process of claim 3 wherein said extraction step is effected at a temperature of about 50° to about 60° C.

43. The process of claim 1 wherein said extraction with aqueous calcium salt solution is conducted at a pH of about 5 to about 7.

44. The process of claim 4 wherein said aqueous soy protein solution has a protein concentration of about 10 to about 50 g/L.

45. The process of claim 10 wherein said aqueous diluent has a temperature of about 50° to about 60° C.

46. The process of claim 12 wherein said acidified of soy protein solution and residual soy protein source has a conductivity of about 2 to about 23 mS.

47. The process of claim 14 wherein said heat treatment is effected at a temperature of about 80° to about 120° C. for 10 seconds to about 5 minutes.

48. The process of claim 15 wherein the heat treated acidified mixture of soy protein solution and residual soy protein source is cooled to about 50° to about 60° C. for further processing.

49. The process of claim 17 wherein the heat treatment is effected at a temperature of about 80° to about 120° C. for about 10 seconds to about 5 minutes.

50. The process of claim 18 wherein the heat treated acidified soy protein solution is cooled to a temperature of about 50 to about 60° C. for further processing.

51. The process of claim 21 wherein said membrane has a molecular weight cut-off of about 5,000 to about 100,000 Daltons.

52. The process of claim 25 wherein said diafiltration is effected using about 2 to about 25 volumes of diafiltration solution.

53. The process of claim 28 wherein the membrane has a molecular weight cut-off of about 5,000 to about 100,000 Daltons.

54. The process of claim 29 wherein said concentration and optional diafiltration step are carried out at a temperature of about 50° to about 60° C.

55. The process of claim 31 wherein said heat treatment is effected at a temperature of about 80 to about 120° C. for about 10 second to about 5 minutes.

56. The process of claim 32 wherein the heat treated soy protein solution is cooled to a temperature of about 50 to about 60° C. for further processing.

57. The process of claim 35 wherein said pasteurization step is effected at a temperature of about 60° to about 65° C. for about 10 to about 15 minutes.

* * * * *